(12) United States Patent
Belcher et al.

(10) Patent No.: US 10,436,725 B2
(45) Date of Patent: Oct. 8, 2019

(54) VIRTUAL BARRICADE FOR RADIATION INSPECTION OF PREDEFINED PATHS

(71) Applicant: GEORGETOWN RAIL EQUIPMENT COMPANY, Georgetown, TX (US)

(72) Inventors: Jeb Everett Belcher, Georgetown, TX (US); Jessica Emily Kelley, Eustis, FL (US)

(73) Assignees: GEORGETOWN RAIL EQUIPMENT COMPANY, Georgetown, TX (US); University of Florida Research Foundation, Incorporated, Gainesville, FL (US)

( * ) Notice: Subject to any disclaimer, the term of this patent is extended or adjusted under 35 U.S.C. 154(b) by 323 days.

(21) Appl. No.: 15/623,082

(22) Filed: Jun. 14, 2017

(65) Prior Publication Data
US 2017/0356861 A1 Dec. 14, 2017

Related U.S. Application Data

(60) Provisional application No. 62/349,763, filed on Jun. 14, 2016.

(51) Int. Cl.
*G01V 5/00* (2006.01)
*G01N 23/02* (2006.01)
*G01N 23/203* (2006.01)

(52) U.S. Cl.
CPC ..... *G01N 23/203* (2013.01); *G01N 2223/053* (2013.01); *G01N 2223/32* (2013.01); *G01N 2223/323* (2013.01); *G01N 2223/624* (2013.01); *G01N 2223/646* (2013.01)

(58) Field of Classification Search
CPC ...... G01N 23/04; G01N 23/20; G01N 23/203; G01V 5/0066
See application file for complete search history.

(56) References Cited

U.S. PATENT DOCUMENTS

2019/0187324 A1* 6/2019 Vienne ................ G01V 5/0066

* cited by examiner

*Primary Examiner* — Don K Wong
(74) *Attorney, Agent, or Firm* — Parsons Behle & Latimer

(57) ABSTRACT

A method of operating a radiation inspection system includes identifying a regulatory region along a predetermined path where public access is restricted based upon criteria other than radiation exposure, measuring a radiation exposure level from a radiation source of the radiation inspection system within the regulatory region, irradiating a target within the regulatory region using the radiation source and without erecting a physical barricade, and determining a restricted area around the radiation source. The restricted area corresponds to an area where a radiation exposure rate exceeds a predetermined threshold. The radiation exposure rate may be determined by the radiation exposure level from the radiation source and a speed of the radiation inspection system. The method may include operating the radiation inspection system to dynamically adjust the restricted area so that it does not extend beyond the regulatory region. The radiation inspection system may be moveable along the predetermined path.

20 Claims, 7 Drawing Sheets

RADIATION EXPOSURE LEVELS - 6 FEET ABOVE RAILROAD TIE LEVEL

| DISTANCE FROM RAIL (FEET) | DISTANCE FROM SOURCE (FEET) | | | | | |
|---|---|---|---|---|---|---|
| | 0 | 4 | 8 | 12 | 16 | 20 |
| 4 | 0.63 | 0.80 | 0.20 | 0.16 | 0.51 | 0.16 |
| 8 | 0.26 | 0.31 | 0.12 | 0.16 | 0.12 | 0.07 |
| 12 | 0.29 | 0.21 | 0.16 | 0.14 | 0.11 | 0.08 |

RADIATION EXPOSURE LEVELS - 3 FEET ABOVE RAILROAD TIE LEVEL

| DISTANCE FROM RAIL (FEET) | DISTANCE FROM SOURCE (FEET) | | | | | |
|---|---|---|---|---|---|---|
| | 0 | 4 | 8 | 12 | 16 | 20 |
| 4 | 0.61 | 0.17 | 0.21 | 0.15 | 0.19 | 0.21 |
| 8 | 0.53 | 0.31 | 0.09 | 0.14 | 0.12 | 0.17 |
| 12 | 0.31 | 0.38 | 0.24 | 0.14 | 0.05 | 0.08 |

200# VIRTUAL BARRICADE FOR RADIATION INSPECTION OF PREDEFINED PATHS

CROSS REFERENCE TO RELATED APPLICATIONS

The present application claims the benefit of priority under 35 U.S.C. § 119 to U.S. Provisional Application No. 62/349,763, filed Jun. 14, 2016, entitled "VIRTUAL BARRICADE FOR X-RAY INSPECTION OF PREDEFINED PATHS," the disclosure of which is incorporated herein by reference in its entirety.

BACKGROUND

Field of the Disclosure

The embodiments described herein relate generally to methods of delineating a radiation region of a radiation inspection system and operating the radiation inspection system without a physical barrier. More particularly, the disclosure relates to the use of preexisting markings or regulations to exclude the public from the radiation region.

Description of the Related Art

Railway inspection systems, such as the Aurora $X^i$ system offered by Georgetown Rail Equipment Company of Georgetown, Texas, and systems as disclosed in U.S. Pat. No. 9,031,188, issued on May 12, 2015, and entitled "Internal Imaging System," the disclosure of which is incorporated by reference in its entirety, are used to scan railway track with backscatter x-ray inspection techniques. Known systems may be towed or mounted on a by-rail platform and may move at speeds up to 25 mph. It is recognized that regulatory agencies suggest keeping radiation exposure from these systems ALARA, or "As Low As Reasonably Achievable." However, due to the wide-range of radiation applications, there are no rigidly defined safety practices for achieving this standard.

Known methods of inspecting railway systems include using at least one industrial radiographer to operate the inspection system while one or more additional radiographers establish a physical barricade to exclude non-radiation workers. A physical barricade is established on all sides of the radiation area and has to be continuously manned to ensure no unauthorized entry can occur. As a result, although known rail inspection systems may be capable of inspecting at speeds up to 25 mph and approximately 100 miles per day, operation at these speeds and distances is costly and labor intensive when a physical barricade is used. The physical barricade must be continuously moved and monitored and a large amount of manpower is needed.

SUMMARY

The present disclosure is directed to a method of virtually delineating a radiation region of a radiation inspection system that mitigates and/or overcomes some of the problems and disadvantages discussed above.

The embodiments described herein may enable a radiation inspection system to operate more quickly and with less radiographers. The embodiments described herein may enable a radiation inspection system to operate without a physical barricade. The embodiments described herein may utilize known restrictions along a predetermined path to exclude access to radiation doses above a preselected level.

An embodiment of a method of operating a radiation inspection system along a predetermined path includes setting a virtual barricade and irradiating a target with the radiation inspection system without erecting a physical barricade along the predetermined path. The virtual barricade has a barricade region at or within a predefined region. The radiation inspection system and the target are positioned within the barricade region. The method includes operating the radiation inspection system so a radiation level outside the predefined region does not exceed a predetermined threshold.

The predefined region may be a regulatory region restricting access to the public. The regulatory region may restrict access to the public based upon criteria other than radiation exposure. The regulatory region may be an area at or within a fouling line of a railroad track. The boundary line is positioned no further from the radiation inspection system than the fouling line. The boundary line may be positioned at least one foot within the fouling line. A side of the barricade region may be delineated by a boundary line extending along at least a portion of the predetermined path.

The method may include moving the radiation inspection system along the predetermined path. The method may include operating the radiation inspection system so a radiation level outside the barricade region does not exceed 2 millirem per hour. The method may include having an operator of the radiation inspection system monitor the barricade region and reduce the radiation emitted from the radiation inspection system if a non-operator enters the barricade region. The radiation inspection system may include an interlock system configured to selectively reduce the radiation emitted from the radiation inspection system.

An embodiment of a method of operating a radiation inspection system along a predetermined path includes irradiating a target along a predetermined path with radiation from a radiation inspection system. A portion of the radiation is transmitted through a predefined region and into an area accessible by the public. The method includes measuring a radiation exposure from the radiation inspection system in the area accessible by the public and setting a virtual barricade having a boundary line at or within the predefined region. A radiation level in the area accessible by the public does not exceed 2 millirem per hour.

The predefined region may be a regulatory region where access to the public is restricted based upon criteria other than radiation exposure. The regulatory region may be an area at or within a fouling line of a railroad track. The boundary line may be positioned no further from the radiation inspection system than the fouling line. The boundary line may be positioned at least one foot away from the area accessible by the public. The method may include irradiating a target without erecting a physical barricade in the area accessible by the public. A radiation level between the boundary line and the area accessible by the public may not exceed 2 millirem per hour. The method may include having an operator of the radiation inspection system monitor the virtual barricade and reduce the radiation emitted from the radiation inspection system if a non-operator crosses the virtual barricade. The radiation inspection system may include an interlock system configured to selectively reduce the radiation emitted from the radiation inspection system.

An embodiment of a method of operating a radiation inspection system along a predetermined path includes identifying a regulatory region along the predetermined path where access to the public is restricted based upon criteria other than radiation exposure, measuring a radiation exposure level from a radiation source of the radiation inspection system within the regulatory region, irradiating a target within the regulatory region using the radiation source and without erecting a physical barricade, and determining a restricted area around the radiation source. The radiation inspection system is moveable along the predetermined path. The restricted area corresponds to an area where a radiation exposure rate exceeds a predetermined threshold. The radiation exposure rate is determined by the radiation exposure level from the radiation source and a speed of the radiation inspection system. The method includes operating an intensity level and the speed the radiation inspection system to dynamically adjust the restricted area so that the restricted area does not extend beyond the regulatory region.

DESCRIPTION

Figure 1:
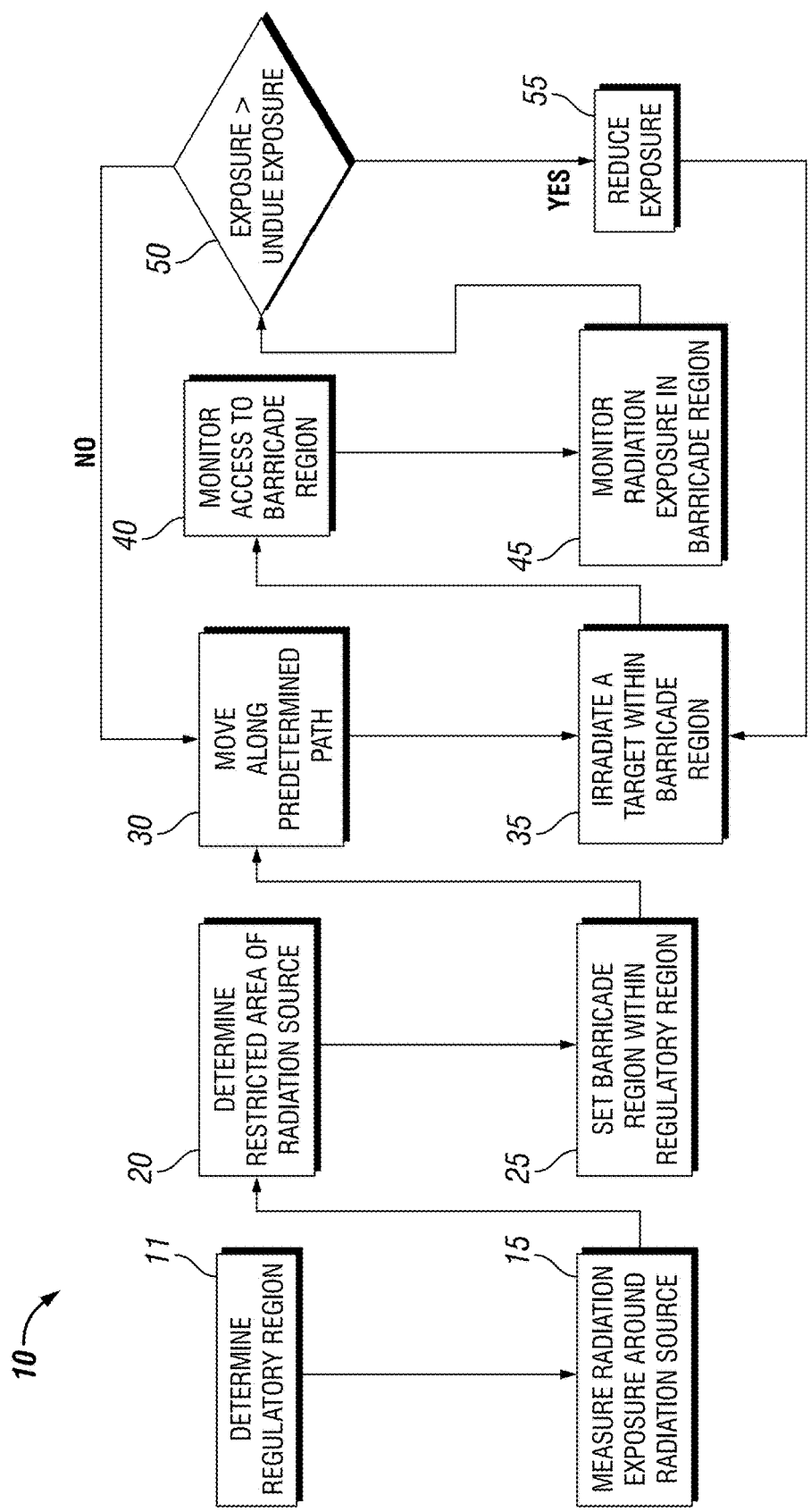
FIG. 1 shows a flow chart of an embodiment of a method of virtually delineating a radiation region of a radiation inspection system.

FIG. 1 shows a flow chart of an embodiment of a method 10 of virtually delineating a radiation region of a radiation inspection system. The method 10 includes determining a location for a virtual barricade. In order to determine a location for the virtual barricade, the method 10 may include the Action 11 of determining a regulatory region along a predetermined path where the public is restricted from accessing. The restrictions may be due to regulatory restrictions unrelated to radiation exposure. The virtual barricade corresponds to the regulatory region. As used herein, the term "public" includes any individual who is not a licensed, monitored radiographer associated with the radiation producing system, and/or the general public. Although the method 10 is discussed with respect to railroad applications, such as the Aurora $X^i$ system operating upon a railroad rack, it is foreseeable that the method 10 is applicable to other radiation inspection systems that operate upon a predetermined path. The virtual barricade may correspond to another predefined and identifiable structure or marking. For example, the method 10 may be applied to a road and the edge of the road, solid white line, or lane identifier might be used as the virtual barricade. Other applications might include areas where an operator may recognize a pre-existing structure or marking as the virtual barricade and act to limit exposure to the public within the virtual barricade.

The method 10 includes the Action 15 of measuring radiation exposure around a radiation source. These measurement are used to determine a restricted area around the radiation source of the radiation inspection system in Action 20. The restricted area may correspond to a region where a radiation exposure threshold may be exceeded. In some embodiments, the restricted area may be determined at a state government level. The Nuclear Regulatory Commission defines a restricted area as "the region around the [radiation] Source in which access is controlled by the operator so that the public does not receive undue exposure." Therefore, the radiation exposure threshold may correspond to a level that causes undue exposure, such as at levels that exceed 2 millirem per hour. The radiation exposure threshold may vary depending on the type of radiation emitted. Accordingly, radiation levels within the restricted area can exceed the radiation exposure threshold if the public is excluded from the restricted area so that they do not receive undue exposure. As discussed above, known methods of restricting access include erecting a physical barricade, such as with rope or cones, to prevent unauthorized access and undue exposure to the public within this area.

The method 10 includes creating a virtual barricade by setting a barricade region in Action 25. The barricade regions is outside or at the edge of the restricted area, wherein the radiation level outside the barricade region is below the radiation exposure threshold to receive undue exposure. The barricade region may be within or at the regulatory region that otherwise restricts access to the public. If the radiation levels outside the regulatory region exceed the radiation exposure threshold to receive undue exposure, then additional shielding may be added to the radiation inspection system or the intensity may be reduced. The barricade region includes a boundary line which extends along at least a portion of the length of the predetermined path, such as a railroad track, upon which the inspection system travels. The distance of the boundary line from the predetermined path may correspond to an edge of the regulatory region or other line along the predetermined path where public access is restricted. The boundary line may be selected so that no physical monitoring by industrial radiographers is needed at or within the boundary line. The boundary line may be the fouling line of a railroad track. The boundary line may be a line between the fouling line and the predetermined path, such as one foot or two feet inside the fouling line.

The Federal Railroad Agency ("FRA") sets the legal standard for the rules of a railroad. While railroad companies in general can create more strict guidelines than the FRA imposes, at the minimum they must at least adhere to those created by the FRA. The FRA defines "Fouling the track" as "the placement of an individual or an item of equipment in such a proximity to a track that the individual or equipment could be struck by a moving train or on-track equipment, or in any case is within four feet of the field side of the near running rail." As used herein, this refers to the "fouling line." Thus, the public is restricted from crossing the fouling line because they may be struck by a moving train or on-track equipment. The use of the fouling line, or a line between the fouling line and the predetermined path, as the boundary line increases the probability that the public will not cross the boundary line and receive undue exposure. Stated another way, by setting the boundary line at the fouling line, a clear line of demarcation that is already recognizable to at least railway workers, such as radiographers and vehicle operators, can be used without erecting a separate physical barrier outside the fouling line.

The barricade region may extend in front of and behind the radiation inspection system along the length of the region being inspected. The barricade region may extend only a preselected distance in front of and behind the radiation inspection system. The preselected distance may correspond to the operator's line of sight or other distances where radiation levels outside the barricade region would not result in undue exposure. The preselected distance may correspond to a minimum distance maintained between vehicles traveling upon the predetermined path. The minimum distance may be 250 feet for rail traversing vehicles. The minimum distance may be determined by a regulatory agency, such as the FRA or the U.S. Department of Transportation. In these cases, the barricade region is dependent upon the location of the radiation inspection system and therefore may move along the predetermined path with the radiation inspection system. The barricade region may extend along the segment of track wherein the inspection system is authorized to move for inspection and may be constrained by working limits such as exclusive track occupancy, inaccessible track, fouling time, or train coordination. Other constraints on the barricade region may include various constraints, such as pilots and lookouts, as would be appreciated by one of ordinary skill in the art having the benefit of this disclosure.

With the barricade region around the radiation source set, the radiation inspection system may move along the predetermined path in Action 30 and irradiate targets within the barricade region to conduct its inspection in Action 35. The operation of the radiation inspection system is controlled so that the radiation exposure levels outside the regulatory region do not exceed a predetermined threshold. The method 10 may include an operator of the radiation inspection system monitoring the barricade region and reducing the radiation emitted from the radiation inspection system if a non-operator crosses the virtual barricade in Action 40. In addition, the operator or the radiation inspection system monitors the radiation exposure levels within the barricade region in Action 45. In Decision 50, it is determined whether the radiation exposure levels exceed undue exposure levels, such as at levels that exceed 2 millirem per hour. If the radiation exposure levels exceed undue exposure levels, then the radiation exposure level is reduced to levels where the restricted area is within the barricade region in Action 55 and inspection and monitoring activities may continue such as irradiating a target within the barricade region in Action 35. If the radiation exposure level does not exceed undue exposure levels, inspection and monitoring activities may continue such as continuing to move along a predetermined path in Action 30.

Figure 2:
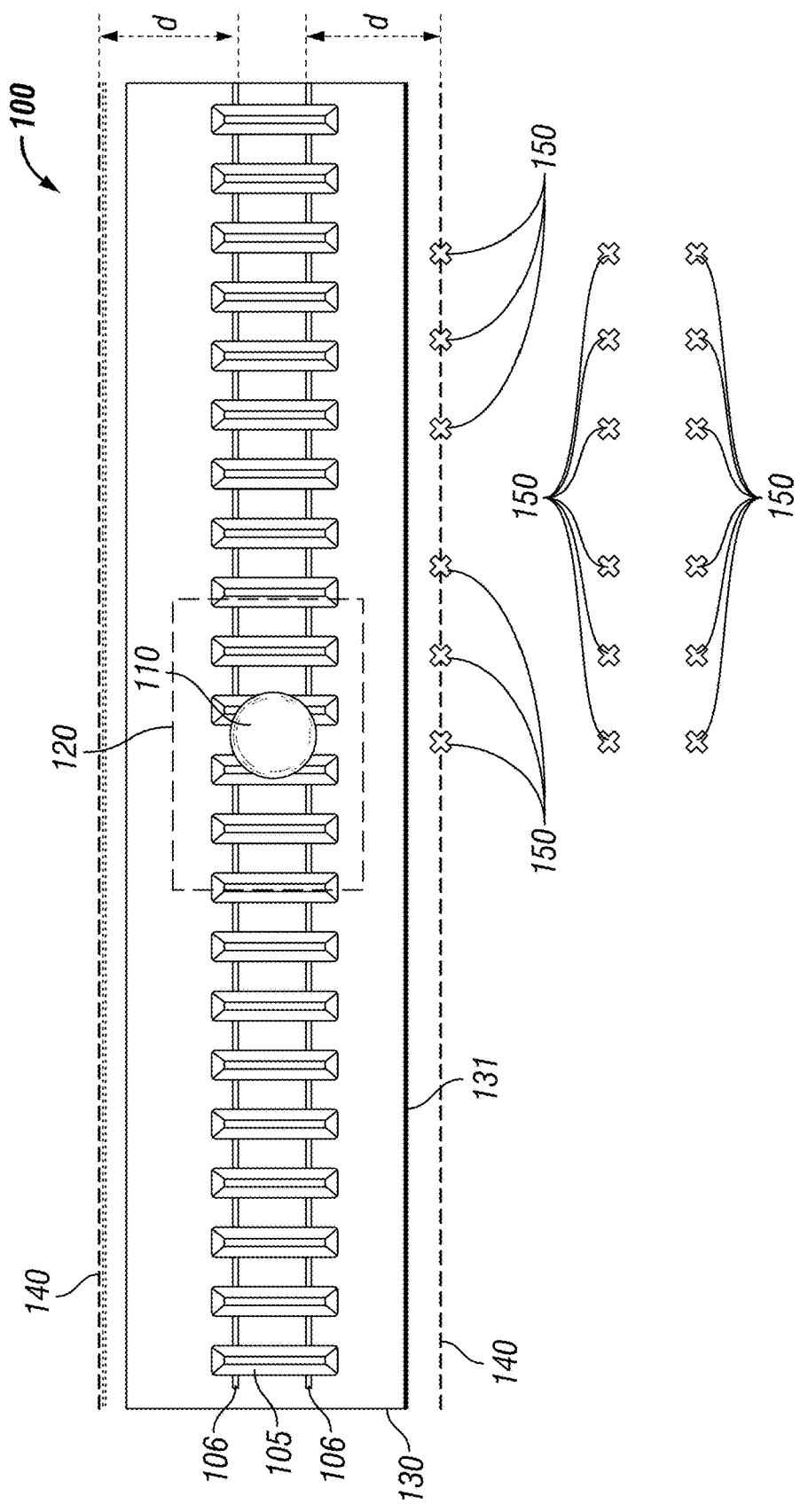
FIG. 2. shows a schematic of an environment of a radiation inspection system confined to travel along a predetermined path.

FIG. 2 shows a schematic of an environment 100 of a radiation inspection system 110 confined to travel along a predetermined path 105, which may be a railroad track. The radiation inspection system 110 includes a radiation source, such as an x-ray tube, neutron source, neutron generator, or gamma ray source. Radiation is emitted from the radiation inspection system 110 to determine internal characteristics of railroad components, such as rails and crossties. Radiation is scattered and otherwise transmitted away from the predetermined path 105 during operation of the radiation inspection system 110. A restricted area 120 of the radiation inspection system 110 exists where undue exposure may occur, such as at levels that exceed 2 millirem per hour. The restricted area 120 may be a dynamic region that is dependent upon the intensity of the radiation source of the radiation inspection system 110, the type of radiation used, the shielding used, and the traveling speed during operation of the radiation inspection system 110. A barricade region 130 is set to separate the restricted area of the radiation inspection system 110 from public space. The barricade region 130 is positioned within a regulatory region, such as inside the fouling line 140 of a railroad track. The regulatory region extends a distance d away from the near running rail 106 of the predetermined path 105. The radiation inspection system 110 may be operated at an intensity level or speed, or with sufficient shielding, such that the restricted area 120 of the radiation inspection system 110 does not extend beyond the barricade region 130. Because the restricted area 120 does not extend beyond the barricade region 130, the barricade region 130 forms a virtual barricade that the public is restricted from crossing and therefore will not receive undue radiation exposure. The barricade region 130 may extend along at least a portion of the predetermined path 105 where the radiation inspection system 110 is authorized to move for inspection and may be constrained by working limits or other preselected distances such that radiation levels outside the barricade region 130 would not result in undue exposure. The outer edge of the barricade region 130 may be referred to as a boundary line 131. The boundary line 131 may be at the fouling line 140 of the predetermined path 105. Alternatively, the boundary line 131 of the barricade region 130 may be positioned between the fouling line 140 and the near running rail 106 of the predetermined path 105 as shown in FIG. 2.

The boundary line 131 of the barricade region 130 may be positioned at or within the fouling line 140 because the public is already restricted from accessing the area between the fouling line 140 and the predetermined path 105. Accordingly, so long as radiation levels outside the barricade region 130 are restricted from exceeding the radiation exposure threshold, the public's exclusion from the area within the fouling line 140 also excludes access to the restricted area 120 of the radiation inspection system 110. Accordingly, the need for radiographers to establish a physical barricade is reduced, or even eliminated. However, a boundary line 131 positioned outside the regulatory region, such as further from the near running rail 106 of the predetermined path 105 than the fouling line 140, may be undesirable because the public may still be permitted to access the barricade region 130 and the restricted area 120 without crossing the fouling line 140. Accordingly, a physical barricade would need to be erected to exclude the public from this area.

Figure 3:
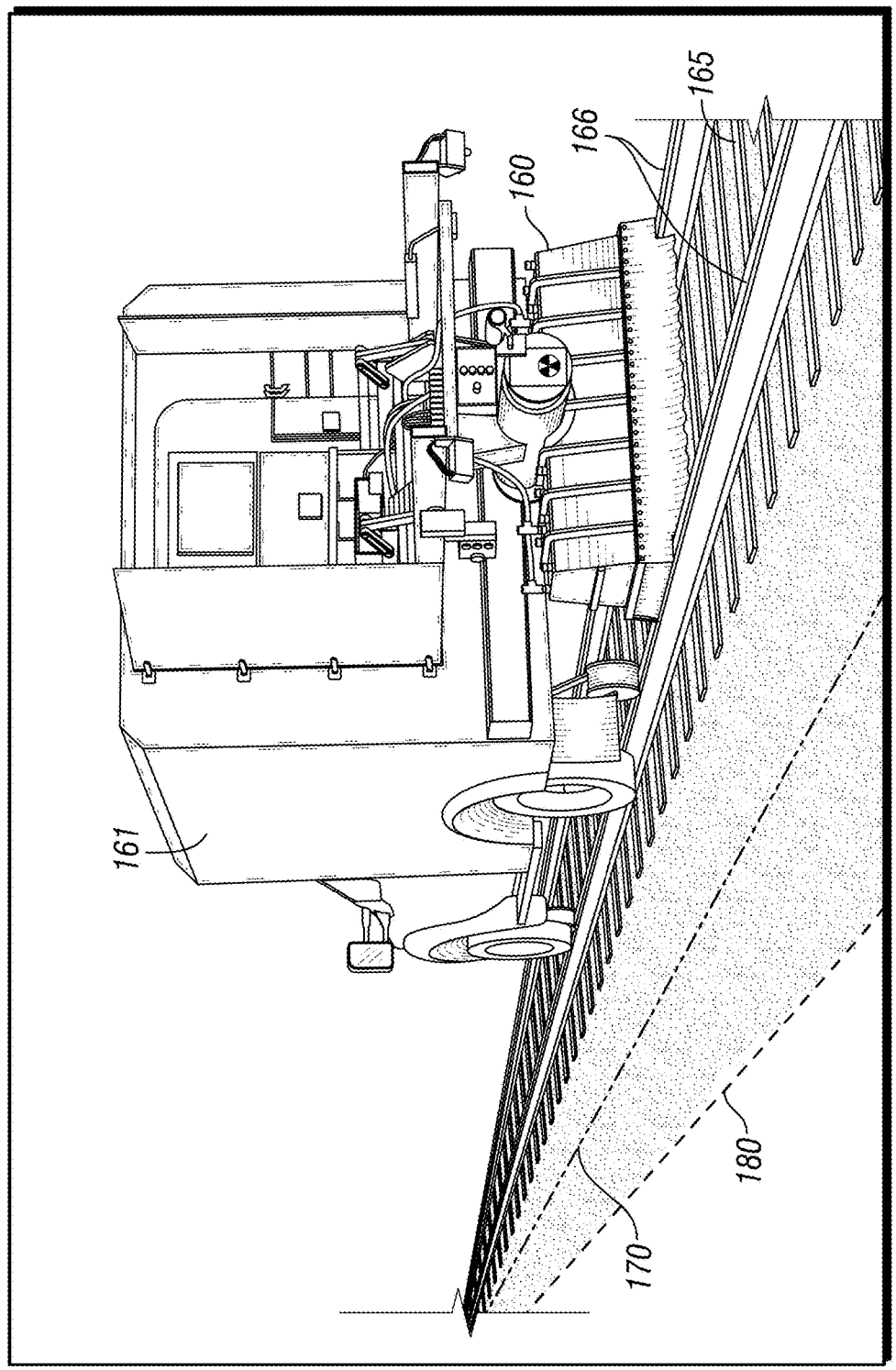
FIG. 3 shows an example of a radiation inspection system with a boundary line of a virtual barricade between the inspection system and the public.

FIG. 3 shows an example of a radiation inspection system 160 traveling along a railroad track 165. As shown, the radiation inspection system 160 may be mounted upon a by-rail vehicle 161 configured to travel on rails 166 of the railroad track 165. Other radiation inspection systems may be towed behind a by-rail vehicle, for example. A fouling line 180 extends along the length of the track 165. Industrial radiographers and other members of the public are restricted from crossing the fouling line 180. A boundary line 170 is positioned at or within the fouling line 180 of the track 165. Industrial radiographers and other members of the public are restricted from crossing the boundary line 170 since it is at or within the fouling line 180 of the track 165. Accordingly, no physical barricade is present.

Figure 4:
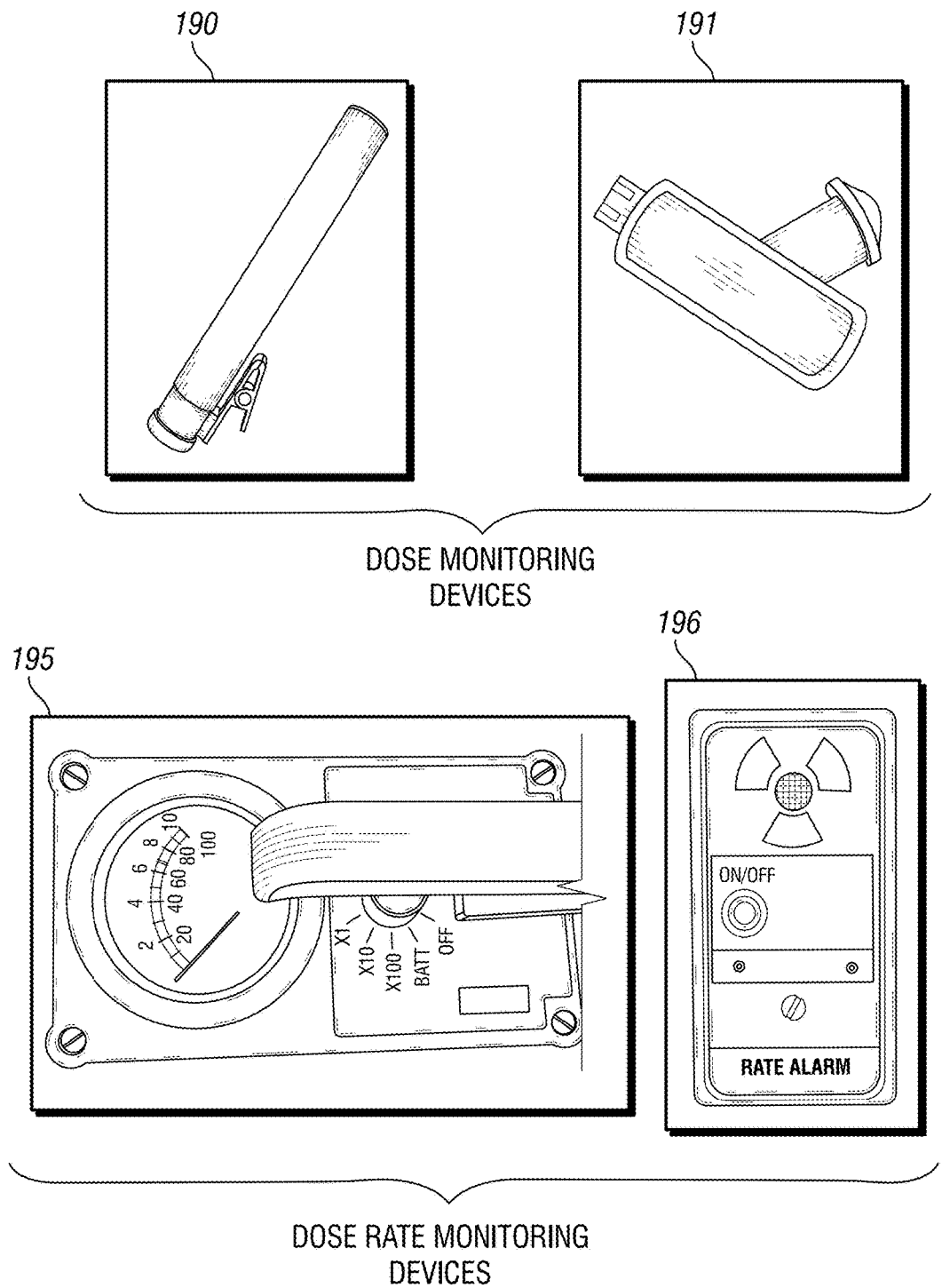
FIG. 4 shows examples of radiation measurement devices.

Referring again to FIG. 2, to establish the restricted area 120 and a boundary line 131 of a barricade region 130, an industrial radiographer may utilize various radiation measurement devices, which may vary depending upon the type of radiation and application. FIG. 4 shows examples of radiation measurement devices that may be used. The radiation measurement devices may be dose monitoring devices such as a dosimeter 190 or a dosimeter badge 191 or dose rate monitoring devices such as a survey meter 195 or a rate alarm 196. The industrial radiographer may initially measure the dose or dose rate at various locations 150 around the radiation inspection system 110. The closest locations 150 to the radiation inspection system 110 may be at the edge of the regulatory region, such as at the fouling line 140. The closest location 150 to the radiation inspection system 110 may be at the boundary line 131. The measurements may be taken in a grid layout with uniform distance between measurement locations 150. The measurements may be repeated at different elevations, such as three feet and six feet, referenced above elements of the predetermined path 105.

Figures 5, 6:
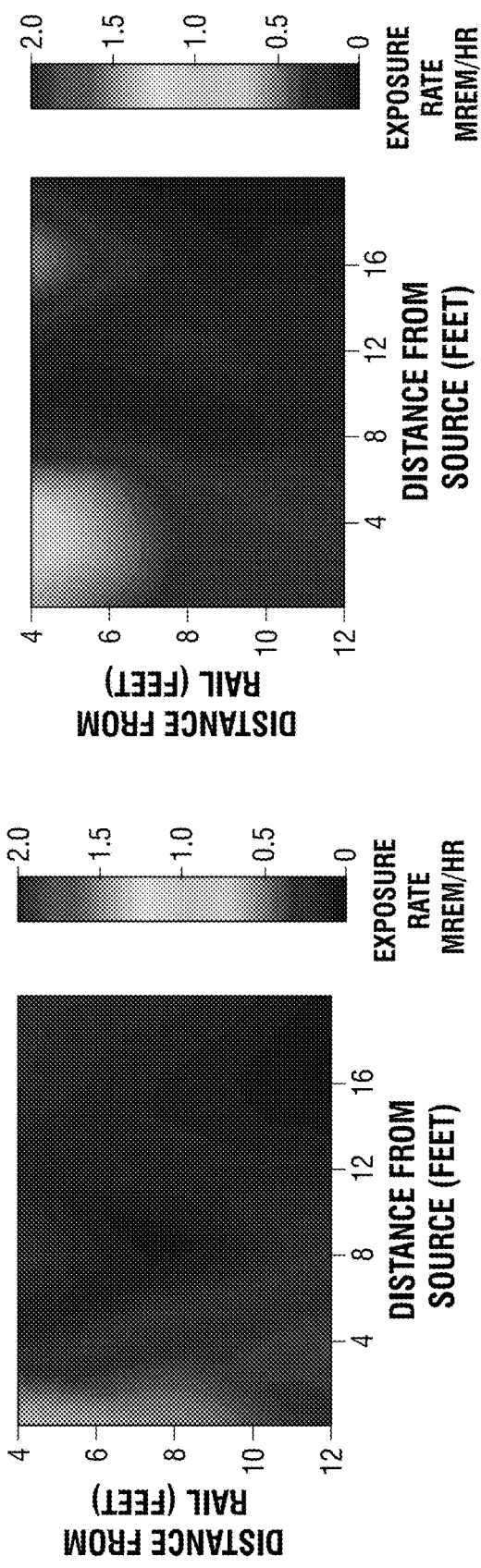
FIG. 5 illustrates radiation exposure at three feet above a railroad tie level of a railroad surrounding a radiation inspection system.
FIG. 6 illustrates radiation exposure at six feet above a railroad tie level of a railroad surrounding a radiation inspection system.

The measurement data collected by the industrial radiographer may be analyzed to determine a radiation exposure profile around the radiation inspection system 110. The radiation exposure profile may be used to adjust the radiation intensity or add additional shielding material in order to avoid undue exposure beyond the fouling line 140, such as at levels that exceed 2 millirem per hour. Table 1 of FIG. 5 shows radiation exposure measured by an industrial radiographer at three feet above the railroad tie level of a railroad track. Measurements were collected in a four foot by four foot grid extending along the predetermined path 105 at selected distances from the radiation source or the rail. It is appreciated that the measurements in Table 1 correspond to the measurement locations 150 shown in FIG. 2. Further, although the data in Table 1 and the locations 150 in FIG. 2 correspond to only to a portion of the area around the radiation inspection system 110, additional measurements may be taken in all directions. FIG. 6 shows a graphical representation of the measurements in Table 1. Table 2 of FIG. 6 shows radiation exposure measured by an industrial radiographer at six feet above the railroad tie level of a railroad. Measurements were collected in the same grid layout as the measurements of Table 1. FIG. 6 shows a graphical representation of the measurements in Table 2.

As may be appreciated from these tables and figures, the radiation exposure levels at four feet from the radiation source, which corresponds approximately to the fouling line 140 (shown in FIG. 2), are below a 2.0 millirem per hour radiation exposure threshold level. Accordingly, the boundary line 131 of the barricade region 130 may be placed at or within the fouling line 140. Because the public is restricted from crossing the fouling line 140, due to other regulations, it will not be exposed to more than 2.0 millirem per hour of radiation so long as they adhere to those regulations. In some embodiments, measurements closer to the radiation inspection system 110 may be taken and the boundary line 131 of the barricade region 130 may be positioned between the fouling line 140 and the near running rail 106 of the predetermined path 105 because the public is still being restricted from crossing the fouling line 140 and accessing the restricted area 120 where radiation may exceed 2.0 millirem per hour. Accordingly, the public is also restricted from entering the barricade region 130 and a radiation inspection system 110 may operate without radiographers erecting a physical barrier. In addition, the radiation inspection system 110 may be operated for longer distances and at faster speeds with reduced costs and reduced risk of radiation exposure to personnel staffing the physical barricades.

Furthermore, the radiation inspection system 110 may be operated such that the restricted area 120 of the radiation inspection system 110 does not extend beyond the barricade region 130 and the boundary line 131 that forms a virtual barricade.

Figure 7:
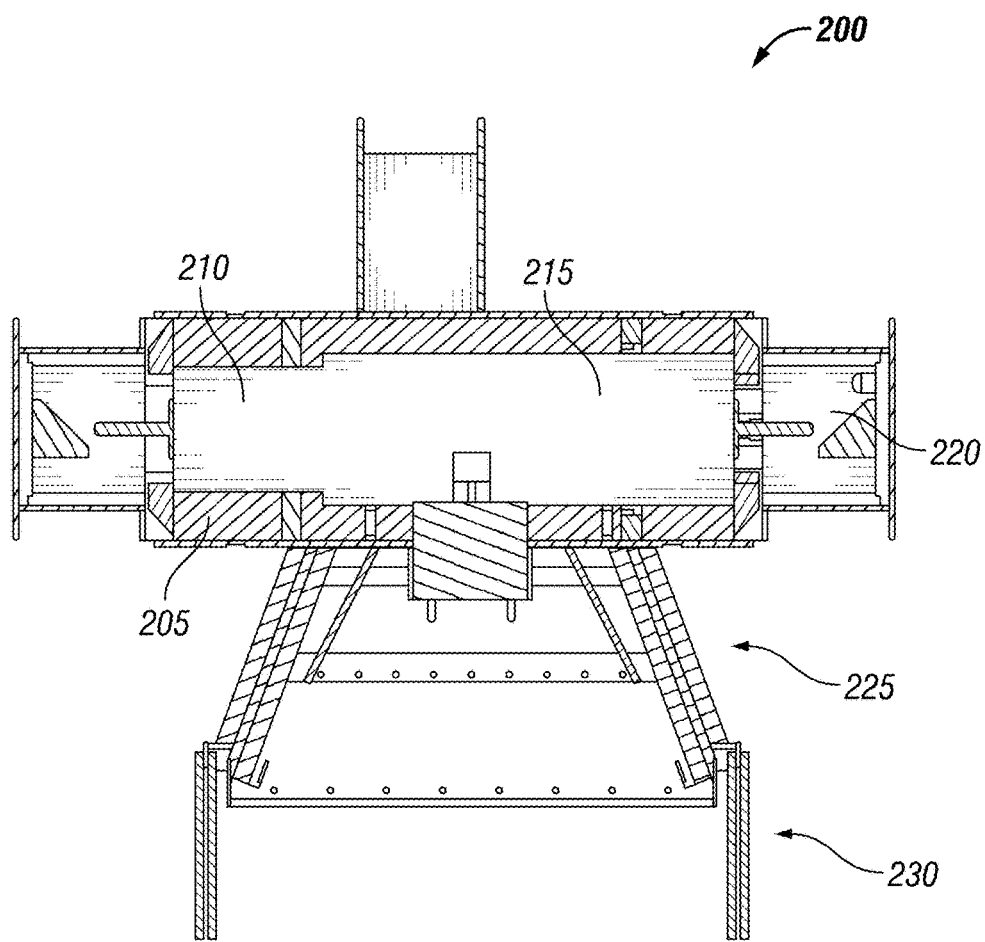
FIG. 7 shows an embodiment of a radiation inspection system with shielding for a radiation source.

A radiation inspection system may include shielding and an interlock system to attenuate the radiation intensity as the radiation inspection system moves away from the target being inspected. The shielding of the radiation inspection system may be comprised of any material that attenuates the radiation. FIG. 7 shows an embodiment of shielding for a radiation source 210 of a radiation inspection system 200. The shielding may include lead shot 215, lead wool 220, lead plate 225, and/or an embedded ceramic 230. Lead shot 215 may be advantageous when a cavity needs to be filled around a radiation producing area. Lead wool 220 may be advantageous when a cavity needs to be filled but cannot be sealed, which would result in a loss of lead shot 215. Plate lead 225 may be advantageous for incorporation into rigid structures such as chamber walls. An embedded ceramic 230, such as SILFLEX manufactured by American Ceramic Technology, Inc. of Escondido Calif., is flexible. Embedded within the flexible ceramic are radiation attenuating materials such as lead, bismuth, or tungsten. These embedded ceramics 230 may be advantageous when radiation shielding needs to be flexible to fill dynamic spaces, or when it needs to be able to "tear away" if struck by foreign objects.

The radiation source 210 may be an x-ray tube housed in a hollow cavity 205. The hollow cavity 205 is filled with lead shot 215. The power cables plug into the x-ray tube at the ends, which are "capped" to create the hollow cavity 205. These caps are filled with lead wool 220 to attenuate any x-rays leaking out the ends. Plate lead 225 may be sandwiched between steel plates to form a rigid "tomb" around the x-ray area. The embedded ceramic 230 may hang below the rigid "tomb" and flexibly move over track components that might be in the way such as rails, ballast, and spikes. The shielding may be designed such that no rigid components are below Association of American Railroads ("AAR") Plate-C compliance envelopes.

Figure 8:
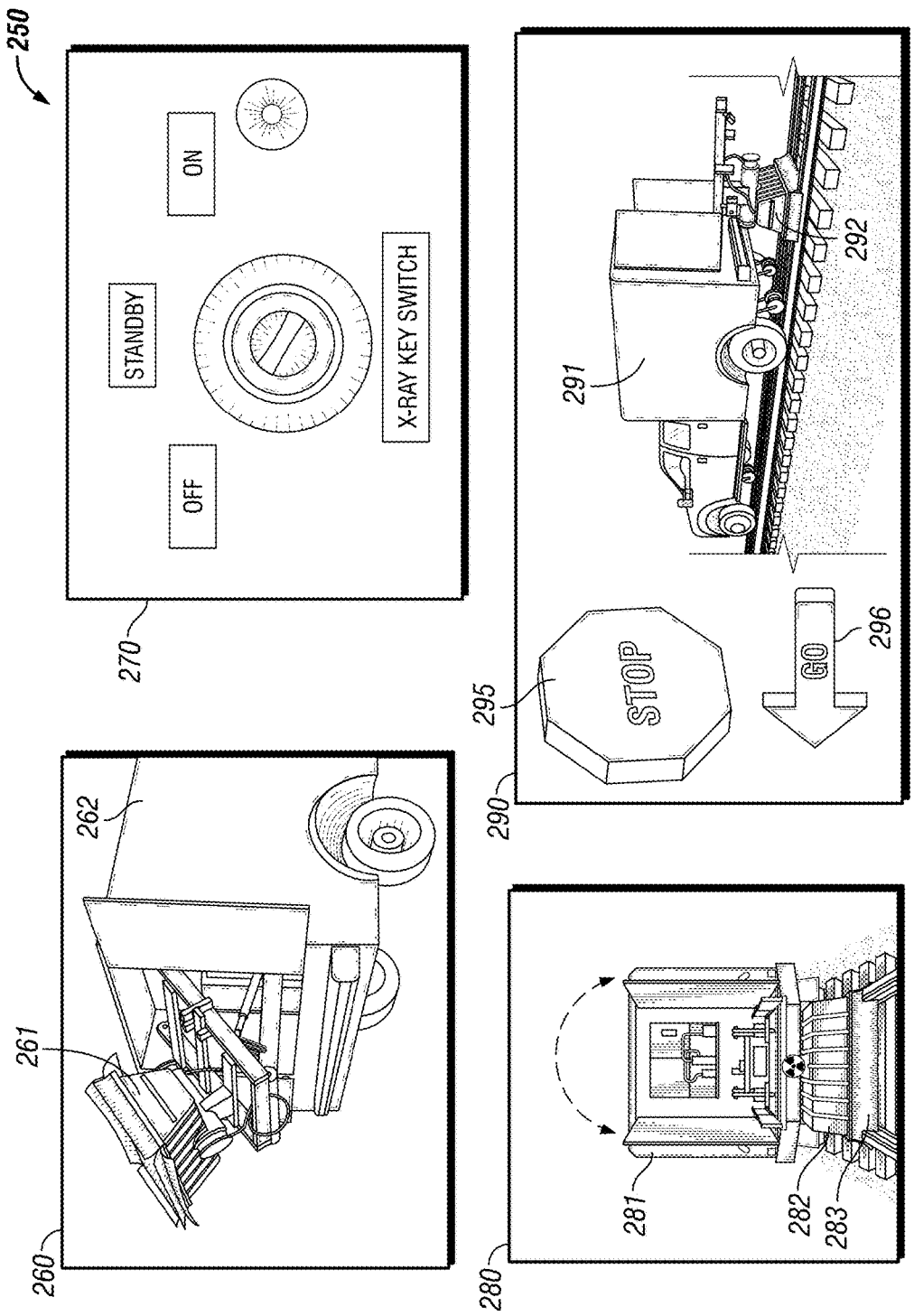
FIG. 8 shows embodiments of programmable triggers that may be used with an interlock system of a radiation inspection system.

FIG. 8 shows embodiments of programmable triggers for an embodiment of an interlock system 250. The interlock system 250 may selectively shield radiation exposure, interrupt operation of the radiation source 210 (shown in FIG. 7), or reduce the radiation expelled from the radiation source 210. The interlock system 250 may be programmed to activate automatically or may be manually operated, such as for emergencies or other non-programmed responses. By way of example, the interlock system 250 may be a position interlock 260, a key interlock 270, an inertial interlock 280, or a speed interlock 290.

A position interlock 260 may ensure the radiation source is pointed in the right direction before x-rays can be emitted. For example, an x-ray system may only operate when the x-ray source 261 is pointed directly at the ground and there is no risk of directly striking a person that is adjacent to the inspection vehicle 262. A key interlock 270 may ensure the radiation system is being operated by an accredited individual (i.e. one who holds a key). This may be a physical key or password for entry into a software program or keypad. An inertial interlock 280 on an inspection vehicle 281 may ensure the radiation system 282 is operating in the correct design specifications. For example, if the inspection vehicle 281 were to rock to one side, then the radiation shielding 283 would no longer be in position to keep radiation from escaping the designated area and may result in undue exposure. A speed interlock 290 on an inspection vehicle 291 may ensure the radiation system 292 is operating within acceptable speed parameters. If a radiation system 292 is moving too slow, then more radiation accumulates in the vicinity of the scan. The speed interlock 290 may activate a stop condition 295 if the scanning speed drops below a minimal scanning speed to ensure that radiation levels are below minimum thresholds. If the scanning speeds are above the minimal scanning speeds, then a go condition 296 is activated to allow further irradiation and inspection. For example, the speed interlock 290 may monitor the speed of travel and the radiation intensity of the radiation inspection system to determine the rate of exposure.

If the rate of exposure at the boundary line 131 or the fouling line 140 (shown in FIG. 2) is determined or predicted to exceed the radiation exposure threshold, such as 2 millirem per hour, the interlock system 250 may be actuated to contain or otherwise reduce radiation levels and thereby reduce the size of the restricted area 120 (shown in FIG. 2). Accordingly, the restricted area 120 can be dynamically modified so that the exposure levels outside of the barricade region 130 (shown in FIG. 2) are maintained below the radiation exposure threshold and the radiation inspection system 110 (shown in FIG. 2) may continue to operate without a physical barrier.

Although this disclosure has been described in terms of certain preferred embodiments, other embodiments that are apparent to those of ordinary skill in the art, including embodiments that do not provide all of the features and advantages set forth herein, are also within the scope of this disclosure. Accordingly, the scope of the present disclosure is defined only by reference to the appended claims and equivalents thereof.

What is claimed is:

1. A method of operating a radiation inspection system along a predetermined path, the method comprising:
    setting a virtual barricade having a barricade region at or within a predefined region, the radiation inspection system being positioned within the barricade region;
    irradiating a target within the barricade region with the radiation inspection system without erecting a physical barricade along a predetermined path; and
    operating the radiation inspection system so a radiation level outside the predefined region does not exceed a predetermined threshold.

2. The method of claim 1, wherein the predefined region is a regulatory region restricting access to the public.

3. The method of claim 2, wherein the regulatory region restricts access to the public based upon criteria other than radiation exposure.

4. The method of claim 3, wherein the regulatory region is an area at or within a fouling line of a railroad track.

5. The method of claim 4, wherein a side of the barricade region is delineated by a boundary line extending along at least a portion of the predetermined path, the boundary line being positioned no further from the radiation inspection system than the fouling line.

6. The method of claim 5, wherein the boundary line is positioned at least one foot within the fouling line.

7. The method of claim 1, further comprising moving the radiation inspection system along the predetermined path.

8. The method of claim 1, wherein operating the radiation inspection system so a radiation level outside the predefined region does not exceed a predetermined threshold comprises operating the radiation inspection system so a radiation level outside the barricade region does not exceed 2 millirem per hour.

9. The method of claim 1, wherein an operator of the radiation inspection system monitors the barricade region and reduces the radiation emitted from the radiation inspection system if a non-operator enters the barricade region.

10. The method of claim 1, wherein the radiation inspection system includes an interlock system configured to selectively reduce the radiation emitted from the radiation inspection system.

11. A method of operating a radiation inspection system along a predetermined path, the method comprising:
    irradiating a target along a predetermined path with radiation from a radiation inspection system, wherein a portion of the radiation is transmitted through a predefined region and into an area accessible by the public;
    measuring a radiation exposure from the radiation inspection system in the area accessible by the public; and
    setting a virtual barricade having a boundary line at or within the predefined region, wherein a radiation level in the area accessible by the public does not exceed 2 millirem per hour.

12. The method of claim 11, wherein the predefined region is a regulatory region where access to the public is restricted based upon criteria other than radiation exposure.

13. The method of claim 12, wherein the regulatory region is an area at or within a fouling line of a railroad track.

14. The method of claim 13, wherein the boundary line is positioned no further from the radiation inspection system than the fouling line.

15. The method of claim 11, wherein the boundary line is positioned at least one foot away from the area accessible by the public.

16. The method of claim 11, wherein the irradiating a target comprises irradiating a target without erecting a physical barricade in the area accessible by the public.

17. The method of claim 11, wherein a radiation level between the boundary line and the area accessible by the public does not exceed 2 millirem per hour.

18. The method of claim 11, wherein an operator of the radiation inspection system monitors the virtual barricade and reduces the radiation emitted from the radiation inspection system if a non-operator crosses the virtual barricade.

19. The method of claim 11, wherein the radiation inspection system includes an interlock system configured to selectively reduce the radiation emitted from the radiation inspection system.

20. A method of operating a radiation inspection system along a predetermined path, the method comprising:
    identifying a regulatory region along a predetermined path where access to the public is restricted based upon criteria other than radiation exposure;
    measuring a radiation exposure level from a radiation source of a radiation inspection system within the regulatory region, the radiation inspection system being moveable along the predetermined path;
    irradiating a target within the regulatory region using the radiation source and without erecting a physical barricade;
    determining a restricted area around the radiation source, the restricted area corresponding to an area where a radiation exposure rate exceeds a predetermined threshold, the radiation exposure rate being determined by the radiation exposure level from the radiation source and a speed of the radiation inspection system; and
    operating an intensity level and the speed the radiation inspection system to dynamically adjust the restricted area so that the restricted area does not extend beyond the regulatory region.

* * * * *